United States Patent [19]

Cray

[11] 4,133,200
[45] Jan. 9, 1979

[54] APPARATUS FOR TESTING LUBRICANTS

[75] Inventor: Daniel G. Cray, Ris Orangis, France

[73] Assignee: The British Petroleum Company Limited, Sunbury-on-Thames, United Kingdom

[21] Appl. No.: 845,372

[22] Filed: Oct. 25, 1977

[30] Foreign Application Priority Data

Oct. 22, 1976 [FR] France ............................... 76 31973

[51] Int. Cl.² ......................... G01N 3/56; G01N 19/02
[52] U.S. Cl. ........................................... 73/10; 73/64
[58] Field of Search ........................................ 73/9–10, 73/64

[56] References Cited

U.S. PATENT DOCUMENTS 3,033,019 5/1962 Oliver ........................................ 73/9
3,401,550 9/1968 Tarpinian et al. ........................ 73/10

OTHER PUBLICATIONS

Kurz, P. F., Useful Friction Recorder; American Journal Physics, vol. 24, No. 3, Mar. 1956.
Wood Block Tests Oiliness of Oil; Popular Science Monthly, Sep. 1930.

Primary Examiner—Charles Gorenstein
Attorney, Agent, or Firm—Morgan, Finnegan, Pine, Foley & Lee

[57] ABSTRACT

Apparatus suitable for the assessment of lubricants for the slides of machine tools, comprises a fixed slide carrier block, a moving slide block, and a drive block moving parallel to the slides at constant speed, under the action of a motor. The drive block carries a bracket with a lever which makes it possible to load the moving slide block and has a compressible elastic element to push the moving slide block. A comparator dial and an electric displacement sensor are connected to a recorder, so as to display and record the relative movements of the fixed and moving slide blocks.

3 Claims, 5 Drawing Figures

APPARATUS FOR TESTING LUBRICANTS

The present invention relates to an apparatus which makes it possible to assess, and in particular to visualise, to measure and to record, the lubricating properties of lubricants.

Modern machine tools are all equipped with slides which may be longitudinal, transverse, vertical or occupy any other position in space. These slides are very important units of machine tools because they are involved to the positioning of the tool. These slides, which may be of different designs and compositions (e.g. the pairs of materials may be cast iron/cast iron, cast iron/steel, steel/steel, plastic/steel, bronze/steel, etc.) have to be lubricated correctly because the efficiency of the machines is adversely affected, if the relative displacement as between the fixed slide and the moving slide is irregular. Such an irregular relative displacement is found particularly in the form of an advance movement known as "stick-slip." This stick-slip advance movement also has other adverse effects besides imperfect machining, e.g. a premature wear of the slides and of all the other parts of the machine, a very rapid destruction of the tools, an appreciable reduction in the capacities of machining of machine tools, rates of production, etc.

Up to the present time, the choice of lubricants for such slides has been carried out empirically in the absence of representative means for testing under actual conditions of service.

Certainly there exist test machines which make it possible to assess the anti-friction properties of the oils used for the lubrication of the slides of machine tools. These machines are for the most part based on the A.S.T.M. (American Society for Testing and Materials) machine which was introduced into the A.S.T.M. standards in 1970 under the designation D-2877-70. The principal drawbacks of these known machines are that their slides are of very definite designs (shape, surface, profile) which do not correspond to those of the slides of machine tools and that they are compulsorily made of cast iron. It is therefore not possible by means of such a machine to reproduce faithfully the conditions of operation on machine tools, so that the results supplied by a test on such a machine cannot be transposed direct to the slides of a machine tool.

Furthermore, these known machines do not make it possible either to visualise or to record the conditions of friction and in particular the stick-slip phenomenon when it occurs.

Other friction test machines also exist but these are more particularly designed for investigating the phenomena of slipping at high speed, which is not a problem with the slides of machine tools.

Finally, although it would not be unthinkable to use a machine tool itself for testing oils for slides, this would represent a considerable loss of production and it would be very difficult to test rapidly and at low expense various pairs of materials for slides. The object of the present invention is to overcome the drawbacks of known test machines and to provide an apparatus which makes it possible to show, namely to visualise, measure and even record, the conditions of static and kinetic friction of slides consisting of pairs of different materials and between which there is interposed a film of lubricant, this being done in a rapid manner and with a very high degree of reproducibility.

These aims are attained according to the invention by an apparatus for the assessment of the lubricating properties of lubricants comprising one or more fixed slides and one or more moving slides which can move on the fixed slide or slides with the interposition of a film of lubricant, means for applying a pressure between the moving slide or slides and the fixed slide or slides, and also means for determining the resistance opposed to displacement of the moving slide or slides. This apparatus comprises, in combination, a fixed slide carrier block, a moving slide carrier block, a drive block for the moving slide book, a compressible elastic element placed between the drive block and the moving slide block, and measuring means for determining, from the compression of the elastic element, that is to say from the relative displacement of the drive block and the fixed slide carrier block, the friction of the moving slide block on the fixed slide carrier block.

Preferably both the fixed slide carrier block and the moving slide block are interchangeable and their slides may be of different materials, the slides of one of the blocks having a profile which is complementary to those of the other block. The slides of the moving slide block are shorter than the slides of the fixed slide block. The drive block can move at constant speed, parallel to the slides of the slide blocks.

Furthermore, the device includes means for loading the moving slide block. Perferably these means consist of a bracket fixed on the drive block in such a way that its arm projects in the direction of the slide blocks, a lever extending parallel to the slides above the slide blocks from the free end of the arm of the bracket on which it is articulated, this lever resting on a roller on the moving slide block and being capable of being loaded by means of a weight which can be hooked in different positions between the roller and the free end of the lever.

Other characteristics and advantages of the invention will appear from the description given below of one embodiment of an apparatus according to the invention. The invention is illustrated with reference to the attached drawings in which.

Figure 1:
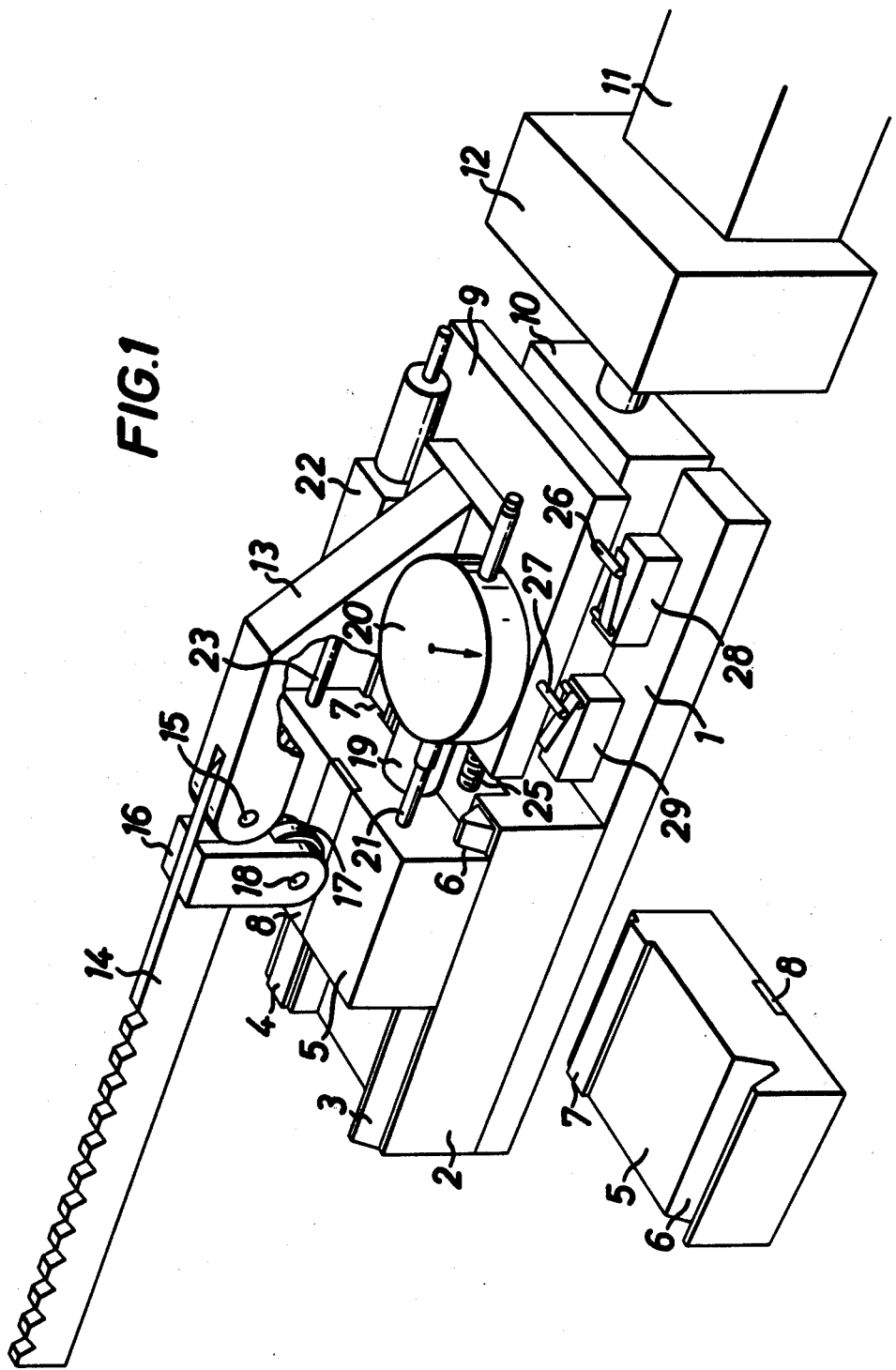
FIG. 1 is a perspective view of an apparatus according to the Invention.

The apparatus illustrated in FIG. 1 comprises a base plate 1 on which there is mounted a fixed slide carrier block 2. This removable block 2 carries on the top two longitudinal slides 3, 4. The slide 3 has a V-shaped profile and the slide 4 is flat.

On the slide carrier block 2 there is placed a moving slide block 5, shorter than block 2 and also having two longitudinal slides 6, 7, the profile of which are complementary to that of slides 3 and 4. The block 5 is placed on the block 2, with its slides 6, 7 turned downwards, facing slides 3, 4 of block 2. It has on its top a rolling track 8, the function of which will be described in greater detail below.

In the extension of the fixed slide carrier block 2 there is mounted a drive block 9 adapted to move by displacement parallel to the slides 3, 4 and 6, 7 on a guide system (not shown in the drawing) with low friction (e.g. rails with rollers) on a transmission gear block 10. The displacement of the block 9 is carried out by means of a precision screw assembly mounted on bearings, from a motor reducing gear 11 with a speed variator (not shown in the drawing). Furthermore, a rapid return mechanism 12 is provided between the transmission gear block 10 and the motor reducing gear 11.

The drive block 9 has a bracket 13 which extends parallel to the slides 3, 4 and 6, 7 above the slide carrier blocks 2 and 5. On the free end of the arm of the bracket 13, lever 14 is articulated around a horizontal spindle 15. The lever 14 is notched from about the middle of its length as far as its free end so as to make it possible to hang weights in different positions, and in the vicinity of its end which articulates on the bracket 13 it has a plate support 16 on which a roller 17 is mounted so as to rotate around a horizontal spindle 18. The roller 17 rests on the rolling track 8 of the moving slide block 5.

The drive block 9 also carries on its face adjacent to the moving slide block 5 an elastic element 19 which is compressible Finally the block 9 carries on its top a comparator dial 20 and an electric displacement sensor 22, the feelers of which, 21 and 23 respectively, extend beyond the block 9 in the same direction as the element 19. The sensor 22 is connected to a source of electrical current and to a variable speed drum recorder and has a number of different sensitivities which makes it possible to choose the amplification of the signals emitted. (This electrical current supply and recorder are not shown in the drawing).

A retractable stop 25 taking the form of a screw is provided on the side of the drive block 9 facing the moving slide block 5, this stop serving for the purpose of adjusting the zero position.

Finally, the drive block 9 has on one side two fingers 26, 27 operating microswitches 28, 29 acting as fixed limit switches on the base 1.

The mode of operation of the apparatus illustrated in FIG. 1 is as follows.

The principle of the apparatus lies in the measurement of the differential displacements between the drive block 9 which is advanced at a constant speed and the moving slide block 5, the regularity of advance of which is a function of the properties of lubrication of the lubricant applied berween the slides 3, 4 and 6, 7.

After choosing the blocks 2 and 5 from suitable materials, the lubricant to be tested is placed on the surfaces of contact of these slides. The moving slide block 5 is loaded, by hooking on a given weight at an appropriate point in the lever, so as to obtain the specific pressure chosen (generally less than 10 bars, preferably between 0.15 and 3.5 bars).

The speed variator (not shown in the drawing) is regulated so as to impart to the drive block 9 a uniform rectilinear movement at a constant speed which has been pre-selected and is less than 1 meter per minute and is preferably between 0 and 12 mm per minute.

As the moving slide block 5 offers a resistance to its advance on the fixed slide carrier block 2 (static friction), the elastic element 19 via which the drive block 9 pushes the moving slide block 5 is compressed.

Three possibilities then exist:
(a) the energy accumulated by the elastic element becomes sufficient to overcome the static friction of the moving slide block, which is projected in the direction of the thrust, and then stops when its resistance to advancement is once again greater than the available energy accumulated by the elastic element, which, under the thrust of the drive block, again accumulates an increasing quantity of energy liberated when it becomes greater than the resistance to advance opposed by the moving slide block, so that the latter is once again projected forwards, and so on.

Figure 2:
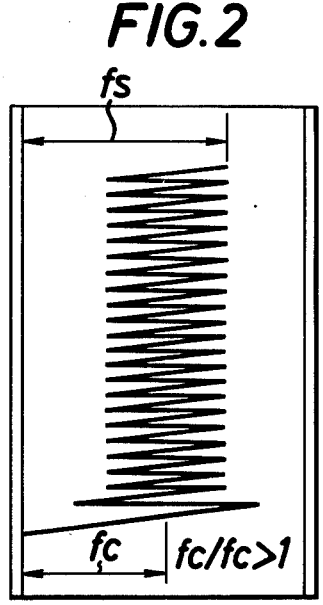
FIGS. 2 to 5 represent four recordings of examples obtained with the apparatus according to FIG. 1 during four tests carried out on different lubricants.

This alteration of accumulation and liberation of energy by the elastic element leads to a stick-slip advance of the moving slide block, which is directly related to the lubricating properties of the product under test: the static friction in this case is greater than the kinetic friction (fs/fc > 1), and, as illustrated in FIG. 2, it is not possible to reach a system of oily lubrication: stick-slip occurs.

Figure 3:
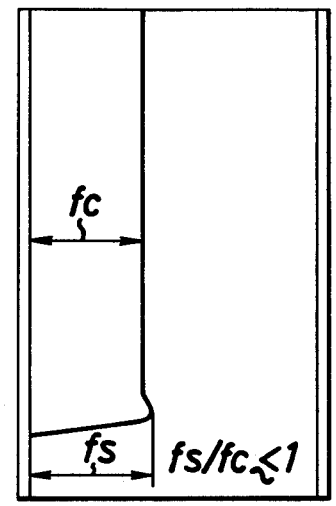

(b) the energy accumulated by the elastic element becomes greater than the resistance opposed by the static friction of the moving slide block, which is then advanced at the same speed as that of the drive block. A point of equilibrium is therefore reached, which causes a regular advance of the assembly of moving blocks: the static friction in this case is less than the kinetic friction (fs/fc > 1) and, as illustrated by FIG. 3, the lubricating properties of the product under test make it possible to obtain an oily lubrication: there is no stick-slip.

(c) during a first period of advance the moving slide block advances as in a), then after a certain travel of varying length behaves as in b). This means that as the bearing surfaces are perfectly deactivated, the activation of these under the double action of the adsorption and chemical activity of the additives is not shown immediately. This activation is directly linked with the nature and the quantity of these additives.

One obtains in this way, at the start, an irregular advance of the moving slide block, then a gradual lessening of the jerks and finally a regular displacement of the moving slide/elastic element/drive block assembly such that:

$$fs/fc > 1 \rightarrow fs/fc \geq 1 \rightarrow fs/fc \leq 1.$$

In this case, the static friction may decrease more or less rapidly and the course of the curve illustrates the faculty which the product under test has of activating the surfaces. The system of oily lubrication is established when $fs/fc \leq 1$.

Figure 4:
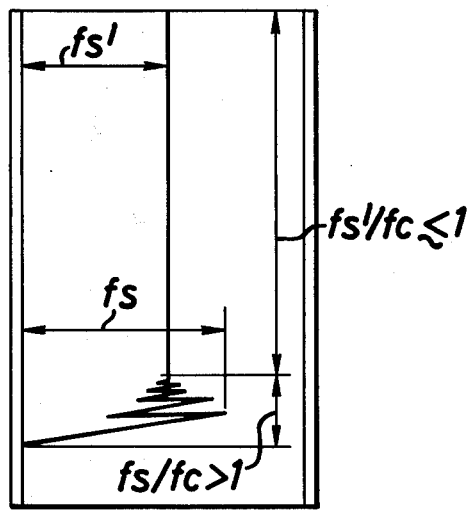

At this stage there exist two possibilities:
(1) The values of fs and fc, for a ratio $fs/fc \leq 1$, are stablised and the energy necessary for driving the moving slide block does not vary any more. In this case, one may estimate that the film of lubricant is totally formed and no longer has the possibility of improving the values of fs and fc (see FIG. 4).
(2) The values of fs and fc, for a ratio $fs/fc \leq 1$ continue to decrease and the energy necessary to drive the moving slide block decreases. In this case, the activation or the surfaces by the lubricant is not yet completed. By continuing the test or by proceeding to a second test, all other things being equal, one can ascertain when the values fs and fc will stablise. When one obtains $fs/fc \leq 1$ for the minimum admissible values of $fs$ and $fc$, this represents the point when the film of lubricant has completely activated the surfaces and when no further improvement is possible (see FIG. 5).

By examining FIGS. 2 to 5 it will be seen that the energy necessary to advance the moving slide block is of greater or lesser magnitude according to whether, all other test conditions being equal, the film of lubricant has adapted itself or not and is formed more or less rapidly.

The values of fs and fc can be measured. In fact the comparator dial 20 indicates by what value (in mm) the elastic element 19 has to be compressed in order to advance the moving slide block 5. The elastic element being standardised (in mm of movement per Newton applied), the difference of relative position between the drive block and the moving slide block is immediately convertible into Newtons.

Furthermore, the values of fs and fc are directly recorded by means of the recorder which is not shown in the drawing, and which responds to the impulses of the electric displacement sensor 22. A simple standardisation makes it possible here also to read direct from the recording the values of $fs$ and $fc$.

The examination of the test recordings on different products under identical conditions or on the same product under different test conditions, makes it possible:
- to verify whether there is a stick-slip effect or not,
- to measure the amplitude of the stick-slip,
- to measure the static friction and the kinetic friction,
- to measure the time necessary to pass (if there is any activation during the test) from a stick-slip advance movement to a regular advance movement.

Figure 5:
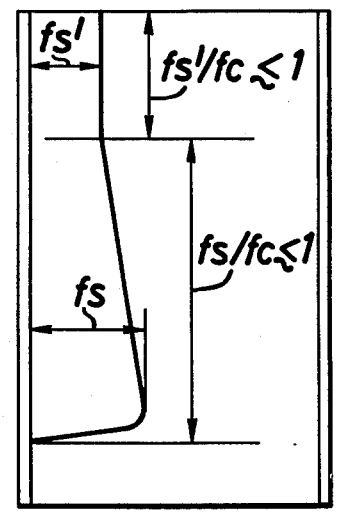

This information makes it possible to determine on the basis of the characteristics of a machine tool what is the best product, bearing in mind the maximum specific pressure admissible between the slides and the minimum advance rates practised. These values may be transferred to the test apparatus and one or more selection tests carried out until a curve which is close to or identical to that of FIG. 3 or FIG. 5 is obtained.

In particular, the test apparatus according to the invention makes it possible:
- to show the phenomenon of stick-slip,
- to assess its magnitude visually,
- to record its amplitude,
- to test a lubricant under varying specific pressures at varying speed,
- and, starting off from these possibilities,
- to verify the performances of one lubricant as compared with another,
- to test a lubricant by varying the pairs of materials used for the slides, and
- having chosen the pair of materials to look for the best lubricant,
- to check very rapidly the lubricating properties of a newly formulated lubricant,
- to determine, on the basis of the requirements of a machine tool, the best viscosity for the lubrication of its slides, the quality level of the oil being correct,
- to measure the speed of formation of a film of lubricant by its powers of adsorption and chemical activation of the surfaces,
- to judge and measure the influence of extraneous elements, e.g. other lubricants, emulsions and machining solutions, etc.,
- to verify the persistence of a film of lubricant over a period of time and according to the distance travelled,
- to test the lubricant properties of an additive at different percentages in solution in a mineral oil or any other base material e.g. grease, gel, alcohol, ester, alkylate, etc.
- to asses the effects of synergism of an additive on one or more others in solution in a mineral oil or any other base material e.g. grease, gel, alcohol, ester, alkylate, etc.,
- to develop new products with the certitude of obtaining on machine tools performances in relation to the qualitative level of lubricants which the apparatus has established,
- to check the different batches of one and the same product.

Other advantages of this apparatus are:
- the excellent repeatability and reproducibility of the tests because the test conditions do not vary during the test (the total surface of the parts in contact of the slides and the specific loads of the slides do not vary over a period of time);
- the perfect reproduction of the conditions of operation of the slides on a machine tool (the V-shaped slides on the apparatus make it possible to take into account the effect of gravity on the spread of the lubricant whilst, on the flat slides, the lubricant is spread mainly by the effect of rolling);
- the small bulk and low weight make the apparatus portable. 9n

I claim:

1. Apparatus for assessing the lubricating properties of lubricants, comprising one or more fixed slides and one or more moving slides which can be displaced on the fixed slide or slides with the interposition of a film of lubricant, means for applying a pressure between the moving slide or slides and the fixed slide or slides, and means for determining the resistance opposed to the displacement of the moving slide or slides on the fixed slide or slides, characterised in that it comprises, in combination,
- at least one fixed slide carrier block adapted to carry slides of different materials
- at least one moving slide carrier block, shorter than the fixed slide carrier block, adapted to carry slides of different materials, said slides of the moving carrier block having profiles complementary to the slides of the fixed slide carrier blocks and adapted to be placed on them
- a drive block capable of moving parallel to the slide block at constant speed, and carrying on the side facing the moving slide block a compressible elastic element by means of which the said drive block acts against the moving slide block and pushes it when driven
- means for loading the moving slide block against the fixed slide block at a constant, pre-determined pressure comprising a bracket on the drive block, a lever articulated on the bracket at one end having a roller thereon and exerting pressure through the roller on the moving slide block, and means for attaching weights to the free end of the lever, and
- means for measuring, from the elastic compression of the elastic element and the relative displacement of the moving slide block and the drive block, the friction of the moving slide block on the fixed slide block.

2. Apparatus for assessing the lubricating properties of lubricants as claimed in claim 1 characterised in that the means for measuring the relative displacement of the moving slide block and the drive block comprises a comparator dial fixed on the drive block connected to a sensor which rests against the face of the moving slide block facing the drive block.

3. Apparatus for assessing the lubricating properties of lubricants as claimed in claim 1 characterised in that the means for measuring the relative displacement of the moving slide block and the drive block comprises an electric displacement sensor device fixed on the drive block and connected to a recording apparatus, the sensor of which rests against the face of the moving slide block facing the drive block.

* * * * *